United States Patent [19]

Stevens

[11] Patent Number: 4,811,743
[45] Date of Patent: Mar. 14, 1989

[54] CATHETER GUIDEWIRE
[75] Inventor: Robert C. Stevens, Williston, Fla.
[73] Assignee: Cordis Corporation, Miami, Fla.
[21] Appl. No.: 40,606
[22] Filed: Apr. 21, 1987
[51] Int. Cl.⁴ .......................................... A61M 25/00
[52] U.S. Cl. ..................................... 128/772; 128/657; 604/170
[58] Field of Search ....................... 128/772, 656–658; 604/280–282, 170

[56] References Cited

U.S. PATENT DOCUMENTS

| | | | |
|---|---|---|---|
| 3,789,841 | 2/1974 | Antoshkiw | 128/772 |
| 3,906,938 | 9/1975 | Fleischhacker | 128/772 |
| 4,215,703 | 8/1980 | Willson . | |
| 4,456,017 | 6/1984 | Miles | 128/772 |
| 4,516,972 | 5/1985 | Samson | 604/282 |
| 4,538,622 | 9/1985 | Samson et al. | 128/772 |
| 4,545,390 | 10/1985 | Leary | 128/772 |
| 4,548,206 | 10/1985 | Osborne | 128/772 |
| 4,619,274 | 10/1986 | Morrison | 128/772 |
| 4,676,249 | 6/1987 | Arenas et al. | 604/282 X |
| 4,719,924 | 1/1988 | Crittenden et al. | 128/772 |
| 4,721,117 | 1/1988 | Mar et al. | 128/772 |

FOREIGN PATENT DOCUMENTS

| | | | |
|---|---|---|---|
| 0014424 | 8/1980 | European Pat. Off. | 128/772 |
| 200430A1 | 8/1984 | European Pat. Off. . | |
| 200430A2 | 8/1984 | European Pat. Off. . | |
| 1119158 | 5/1966 | United Kingdom . | |

Primary Examiner—Kyle L. Howell
Assistant Examiner—Angela D. Sykes
Attorney, Agent, or Firm—Watts, Hoffmann, Fisher & Heinke

[57] ABSTRACT

A catheter guidewire for use in inserting a catheter into a subject. The guidewire includes a center wire core surrounded by a coiled wire sheath that is Teflon coated on an outside surface. The extreme distal end of the rod widens to a sphere. The rod and sheath are pre-bent to a desired form. As the core is rotated inside the sheath, the distal end of the guidewire is re-oriented in the direction of rotation.

11 Claims, 2 Drawing Sheets

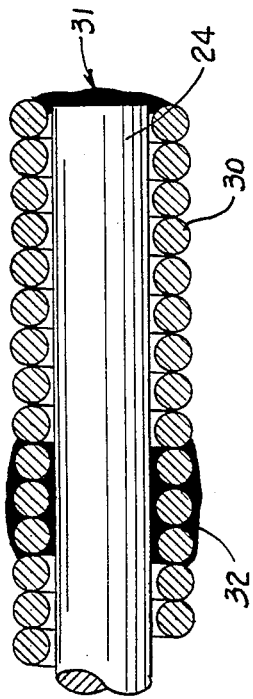
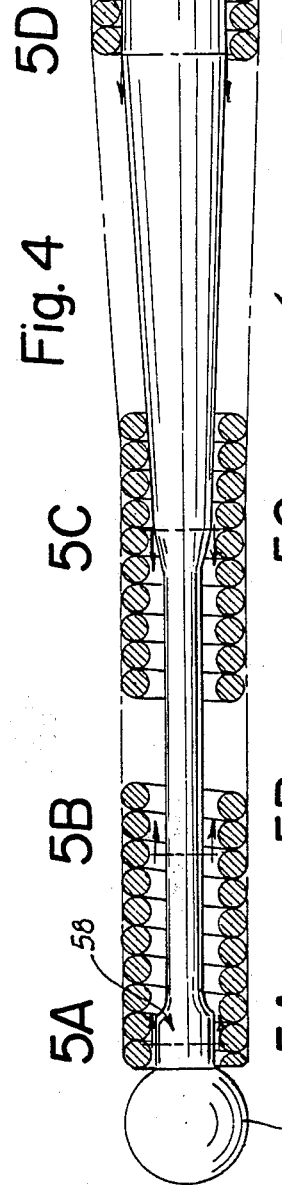
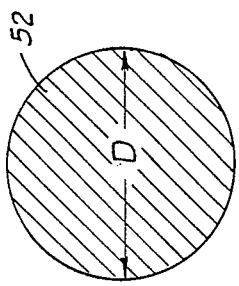
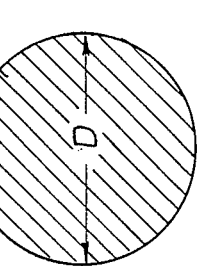
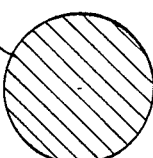
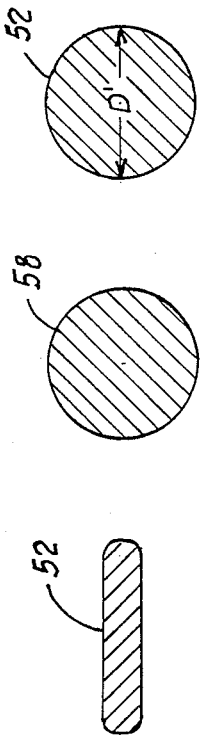

CATHETER GUIDEWIRE

DESCRIPTION

1. Technical Field

The present invention relates to a catheter guidewire to aid in positioning a catheter within a subject.

2. Background Art

Prior art U.S. Pat. No. 4,538,622 to Samson et al. dated Sept. 3, 1985 and U.S. Pat. No. 4,545,390 to Leary dated Oct. 8, 1985 disclose catheter guidewires to aide a physician in properly positioning a catheter within a patient. The guidewire is constructed at least in part of radio-opaque material so that the physician can monitor guidewire movement on a viewing screen as the guidewire is inserted into a patient. The guidewires disclosed in the two aforementioned prior art patents include flexible distal tips which can be pre-bent by a physician into a particular shape and then used in routing a tubular catheter into a patient. The pre-defined shape of the guidewire facilitates entry in branching vessels encountered during insertion of the catheter. The flexible tip allows the guidewire to be inserted without damaging the interior wall structure of the blood vessel. At the distal end of the guidewire, a spring member is soldered or otherwise fixed to a small diameter rod extending the internal length of the guidewire. A major object of the above prior art guidewires is to allow the physician to exert a rotating torque at the proximal end of the guidewire and transmit that torque to the distal end to allow controlled orientation of the guidewire tip during its insertion.

DISCLOSURE OF THE INVENTION

It is an object of the present invention to provide a reliable, easily oriented catheter guidewire to aid a physician during catheterization.

A catheter guidewire constructed in accordance with the invention includes an elongated flexible center core member having an enlarged tip portion at its extreme distal end. The elongated flexible center core member is surrounded by a tightly coiled wire sheath that covers a substantial length of the flexible center member and has an outer diameter small enough to be inserted within a tubular catheter.

To re-orient the distal end of the guidewire the flexible center member is grasped by the physician and rotated within the sheath. As the flexible core member rotates within the sheath, it re-orients the pre-bent distal portion of the guidewire. As the guidewire is pushed forward into the blood vessel, the physician can controllably orient the distal portion of the guidewire to direct the guidewire into branching vessels. Once the distal tip has been guided into these branching vessels, the tubular catheter can be pushed ahead over the guide.

Depending upon the intended application, the distal portion of the catheter guide can define a number of different configurations. In applications where the guide is intended for entry into small diameter blood vessels, the distal portion of the guide must be especially flexible. To achieve this flexibility, both the center member and the outer coiled sheath are tapered. The taper in the coiled sheath is accomplished by using a tapered mandrel during fabrication of the sheath. To add even more flexibility, in an alternate embodiment, the tapered portion of the center rod is flattened on opposite sides in a region near the distal tip portion.

The bend at the distal portion of the guide can either be pre-formed during manufacture or can be adjusted by the physician prior to insertion into the subject. Since the coiled sheath is not physically attached to the center rod at the distal portion of the guide, the sheath is generally passive and does not rotate in response to physician manipulation at the proximal end. Instead, as the center core member rotates within the sheath, it causes the outer sheath to roll over.

From the above it is appreciated that one object of the invention is an improved guide member for facilitating insertion of a catheter for patient examination or treatment. This and other objects, advantages and features of the invention will become better understood from a detailed description of a preferred embodiment which is described in conjunction with the accompanying drawings.

BRIEF DESCRIPTION OF THE DRAWINGS

FIG. 3 is a view as seen from the plane defined by the line 3—3 in FIG. 2;

FIG. 4 is an enlarged diagrammatic view of a distal portion of an alternate guidewire;

FIG. 5A is a section view as seen from the plane defined by the line 5A—5A in FIG. 4;

FIG. 5B is a section view as seen from the plane defined by the lines 5B—5B in FIG. 4;

FIG. 5C is a section view as seen from the plane defined by the lines 5C—5C in FIG. 4; and, FIG. 5D is a section view as seen from the plane defined by the lines 5D—5D in FIG. 4.

BEST MODE FOR CARRYING OUT THE INVENTION

Figure 1:
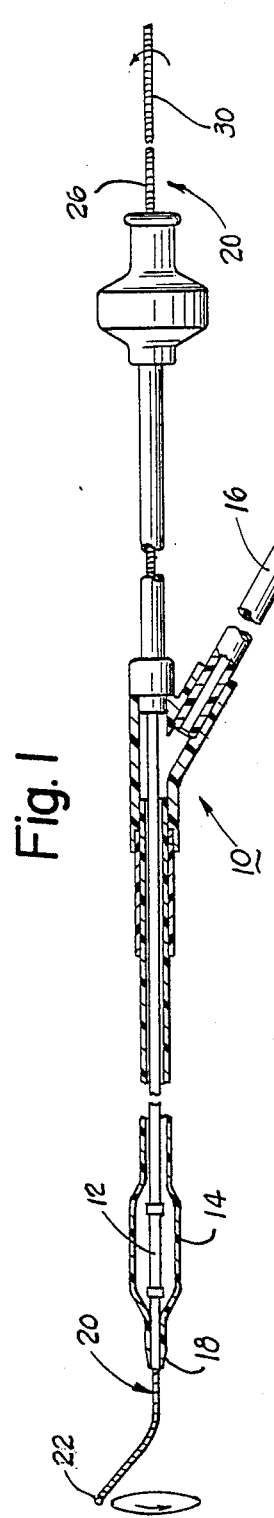
FIG. 1 is a partially sectioned elevation view of a balloon catheter having a guidewire inserted through a center passageway for facilitating catheter insertion.

Turning now to the drawings, FIG. 1 illustrates a balloon catheter 10 for use in conducting an angioplasty procedure to enlarge an obstructed blood vessel. As those familiar with the art of angioplasty are aware, the step of inserting such a catheter within a patient is facilitated by the use of a guidewire 20 for properly positioning the balloon catheter prior to balloon inflation. In the FIG. 1 catheter construction the guidewire 20 extends through a center tube 12 in the balloon catheter 10 and includes a pre-bent configuration at a distal end. As the distal portion of the guide is oriented, the physician monitors movement of the guidewire 20 and directs the distal portion through branching vessels of the cardiovascular system. Once the balloon catheter has been properly positioned with the aid of a guidewire, an inflatable balloon 14 is inflated by applying pressure via a catheter side branch 16 to widen the passageway within the blood vessel of interest.

The use of guidewires is not limited to use with balloon catheters. Guidewires can be also utilized in inserting other catheters for conducting angiographic studies and the like. For these studies, a standard procedure is to insert the guidewire before an angiographic catheter is routed over the guidewire into a blood vessel region of interest.

A guidewire 20 constructed in accordance with the invention is shown inserted through the balloon catheter 10 and extending beyond a distal tip 18 of that catheter. By rotating a proximal portion of the guidewire 20, the physician can re-orient the bent portion at the distal end of the guidewire 20 in a controlled fashion. In particular, the physician can orient an extreme distal tip 22 toward a branching vessel. Once the guidewire is properly oriented, the physician pushes the guidewire 20 ahead and then slides the balloon catheter forward along the guidewire 20.

Figure 2:
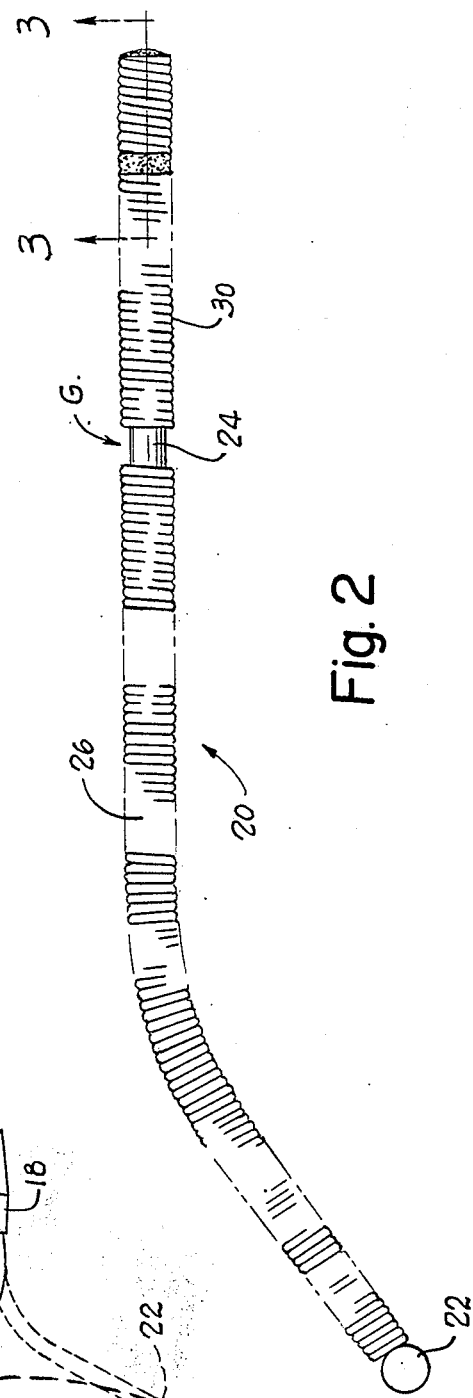
FIG. 2 is an enlarged elevation view of one embodiment of the guidewire.

Turning now to FIG. 2, the guidewire 20 of the invention is seen to include an elongated, generally cylindrical core 24 of stainless steel wire surrounded by a coiled wire sheath 26. The enlarged distal tip portion 22 is physically a part of the center core 24. In a preferred embodiment of the invention, the spherical distal tip 22 is formed by using a TIG (Tungsten Inert Gas) welder to heat the distal end of the core 24 with the coiled sheath 26 in place. The heat of the welder melts the wire core 24 to form a sphere-like distal tip 22 having an outer diameter approximately the same as the outer diameter of the sheath 26 at its distal end.

The guidewire illustrated in FIG. 2 has a uniform diameter the entire length of the guidewire 20. The coiled sheath 26 is constructed from 0.003 inch stainless steel wire which is wound around a uniform diameter mandrel, Teflon coated on its outside surface with a thin (less than 0.001 of an inch) Teflon coating and then removed from the mandrel. The outside diameter of the sheath 26 and distal tip 22 is chosen to fit within the catheter to be positioned with the guidewire. Guidewires having outside diameters ranging from 0.012 to 0.038 inches have been constructed. For the smaller diameter guidewires 0.002 inch stainless steel wire is used in fabricating the sheath 26.

At the proximal end of the guidewire 20, a second coiled sheath 30 extends a short distance over the center core 24 and is physically attached to the core. This second coiled sheath 30 facilitates rotation of the core 24 within the first sheath 26. Physical attachment between the sheath 30 and core 24 is accomplished by welding the two together at an extreme proximal portion 31 (FIG. 3). To prevent the second coiled sheath 30 from unraveling during use, a short segment of the coil 30 is spread apart and solder 32 applied to solder the sheath 30 to a core outer surface. A narrow gap G spaces the two sheaths 26, 30. The width of this gap is no greater than the width of two turns of coil but has been shown as being wider in FIG. 2 for illustration purposes.

Figure 1A:
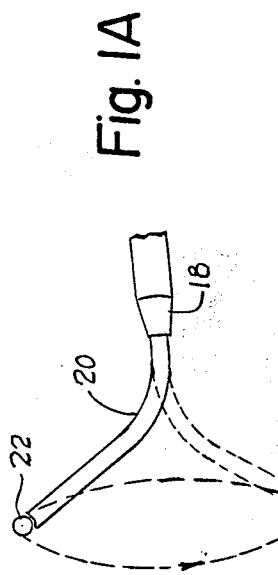
FIG. 1A is an enlarged depiction of an extreme distal portion of the balloon catheter showing the guidewire being re-oriented.

In use, an entryway is cut into a blood vessel and the guidewire 20 routed into the blood vessel by the attending physician. As the guidewire 20 is routed through the vessel, the physician monitors its progress on a viewing screen. As the guide encounters branching vessels, the distal tip 22 of the guidewire 20 can be oriented by rotating the center core 24 within the sheath 26. The curved distal portion of the combined core and sheath 26 is re-oriented (FIG. 1A) by this rotation.

Turning now to FIG. 4, an alternate guidewire 50 having a tapered distal portion is schematically depicted. This guidewire 50 also includes a center core 52, Teflon coated sheath 54 and TIG welded distal tip 56. At a region approximately six inches from the tip 56 the core 52 is machined to define a taper. In one embodiment, the core 52 uniformly tapers from an outer diameter D (FIG. 5D) of 0.014 inches to a diameter D' (FIG. 5C) of approximately 0.005 inch along a length of approximately 4 inches. The 0.005 inch diameter cylindrical core is then flattened along opposite sides (FIG. 5B) by a press to within approximately ⅛ inch of the distal tip 56. As seen in FIG. 4 the outer sheath 54 is also tapered. This is accomplished by use of a tapered mandrel for fabricating the sheath 54. In the illustrated embodiment the sheath 54 tapers from an outer diameter of approximately 0.022 inch to an outer diameter of 0.014 along the flattened portion of the core.

The extreme distal ⅛ portion (approximately ⅛ inch) of the core 52 acts as a bearing 58 as the core 52 rotates within the sheath 54. Since the bearing portion 58 is formed when the taper is machined it has the same diameter as the narrow portion of the tapered core.

The present invention has been described with a degree of particularity. The dimensions given for the guidewires 20, 50 are illustrative and should in no manner limit the scope of the invention. It is the intent, therefore, that the invention include all modifications and alterations of the disclosed design falling within the spirit or scope of the appended claims.

I claim:
1. A guidewire for use in positioning an elongated tubular catheter within a subject comprising:
   (a) an elongated flexible core member longer than the tubular catheter and including a ball shaped tip at a distal end;
   (b) a tightly coiled wire sheath surrounding a substantial length of said elongated flexible core member and having an outer diameter small enough to be inserted within the tubular catheter and an inner diameter at a distal end less than the ball shaped tip of said core member to prevent movement of the ball shaped tip into the coiled wire sheath, said flexible core member rotatable with respect to the tightly coiled wire sheath; and,
   (c) means at a proximal end of said elongated flexible core member for rotating the flexible core member relative to the tightly coiled wire sheath to orient a distal end of said guidewire as the guidewire is moved within the subject.
2. The guidewire of claim 1 wherein the elongated flexible core member has a reduced cross-section portion between a substantially uniform-cross-section portion and said bale-shape tip.
3. The guidewire of claim 2 wherein the reduced cross-section portion of the elongated flexible member is surrounded by a reduced diameter portion of the tightly coiled wire sheath.
4. The guidewire of claim 3 wherein the uniform cross-section portion of the elongated flexible member is circular and the reduced cross-section portion is flattened on opposed sides.
5. The guidewire of claim 2 wherein the reduced cross-section portion of said cone member comprises a tapered region, a region of reduced diameter flattened on opposed sides and a cylindrical bearing region having said reduced diameter, said bearing region adjacent the ball shaped tip.
6. The guidewire of claim 1 wherein the ball shaped tip has a diameter substantially equal to an outer diameter of a distal portion of said sheath.
7. The guidewire of claim 1 wherein the means for rotating comprises a second coiled sheath that sur- rounds and is connected to a proximal end of the elongated flexible core member.

8. The guidewire of claim 1 wherein an outer surface of the sheath is covered with a synthetic coating.

9. A guidewire for positioning a tubular catheter within a subject comprising:
   (a) an elongated flexible core member including a ball shaped tip at a distal end, said core member having a tapered portion at a distal region near the ball shaped tip;
   (b) a tightly coiled wire sheath surrounding a substantial length of said elongated flexible member having an outer diameter small enough to be inserted within the tubular catheter and defining a tapered region along the tapered portion of the core member that defines an inner diameter less than an outer diameter of the ball shaped tip of the core member; and,
   (c) means for rotating a proximal end of said elongated flexible member within the sheath to orient a distal end of said guidewire as the guidewire is moved within the subject.

10. The guidewire of claim 9 wherein the flexible core member includes a uniform cross-section portion flattened on opposed sides adjacent the ball shaped tip.

11. The guidewire of claim 10 wherein the uniform cross-section portion of the core member is flattened along less than its entire length to define a bearing portion adjacent the distal tip to facilitate rotation of the core member within the wire sheath.

* * * * *